United States Patent [19]

Slavik et al.

[11] Patent Number: 4,525,163
[45] Date of Patent: Jun. 25, 1985

[54] INTRAVENOUS SET FLOW CONTROL DEVICE

[75] Inventors: William H. Slavik, Palos Hills; William B. Huber, Oak Park, both of Ill.

[73] Assignee: Nuvatec, Inc., Downers Grove, Ill.

[21] Appl. No.: 406,118

[22] Filed: Aug. 6, 1982

[51] Int. Cl.³ .............................................. A61M 5/16
[52] U.S. Cl. ............................. 604/65; 128/DIG. 12; 128/DIG. 13
[58] Field of Search ............... 128/DIG. 13, DIG. 12; 604/67, 151, 50, 31, 65; 222/40, 59, 64, 253; 340/619; 73/861.41

[56] References Cited

U.S. PATENT DOCUMENTS

| | | | |
|---|---|---|---|
| 3,252,623 | 5/1966 | Corbin et al. | 222/59 |
| 3,609,379 | 9/1971 | Hildebrandt | 128/DIG. 13 |
| 4,018,362 | 4/1977 | Uband | 222/55 |
| 4,286,464 | 9/1981 | Tauber et al. | 340/619 |
| 4,291,692 | 9/1981 | Bowman et al. | 604/50 |
| 4,331,262 | 5/1982 | Snyder et al. | 222/37 |
| 4,354,180 | 10/1982 | Harding | 340/619 |

*Primary Examiner*—Lee S. Cohen
*Assistant Examiner*—Steven Falk
*Attorney, Agent, or Firm*—Willian Brinks Olds Hofer Gilson & Lione Ltd.

[57] ABSTRACT

A controller for an intravenous set is disclosed which operates both to maintain the instantaneous drip rate through a drip chamber included in the IV set at a desired value, and to modify this value repeatedly during the course of an infusion. The desired drip value is modified in accordance with the measured volumetric flow rate through the intravenous set such that if a particular infusion fluid produces abnormally small volume drops in the drip chamber, then the controller automatically increases the drip rate to compensate. In this way, extremely accurate control of the fluid flow rate is obtained without the need for complex infusion pumps. A disclosed embodiment operates to provide separate alarms for open line errors, air in line errors, and occlusion errors.

23 Claims, 19 Drawing Figures

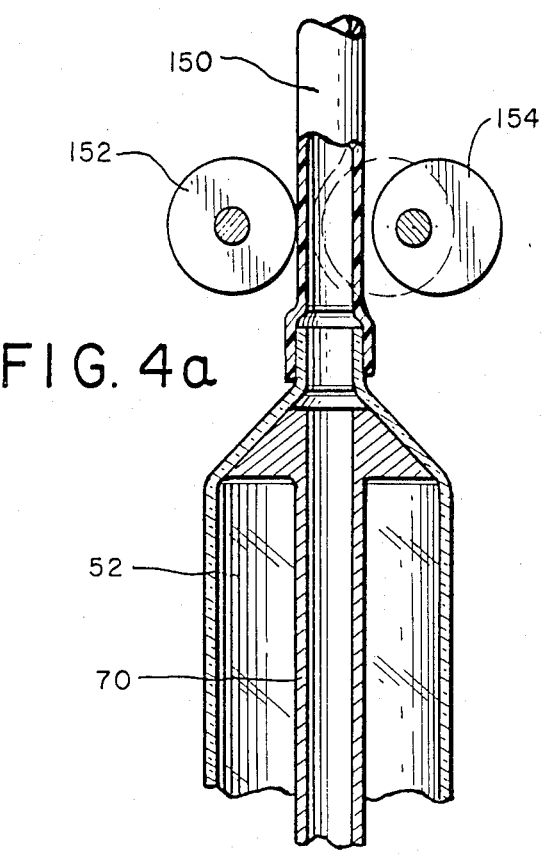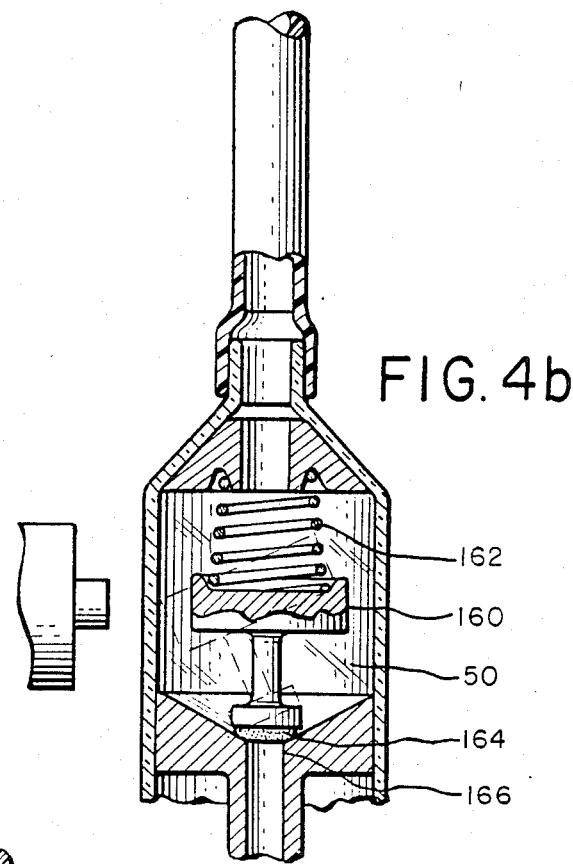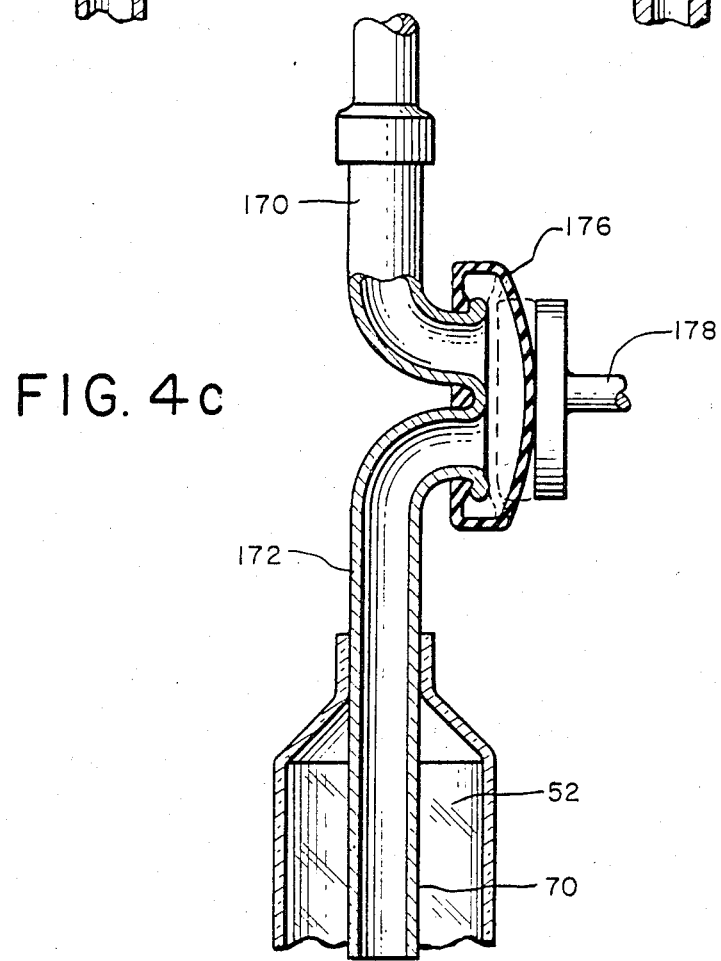

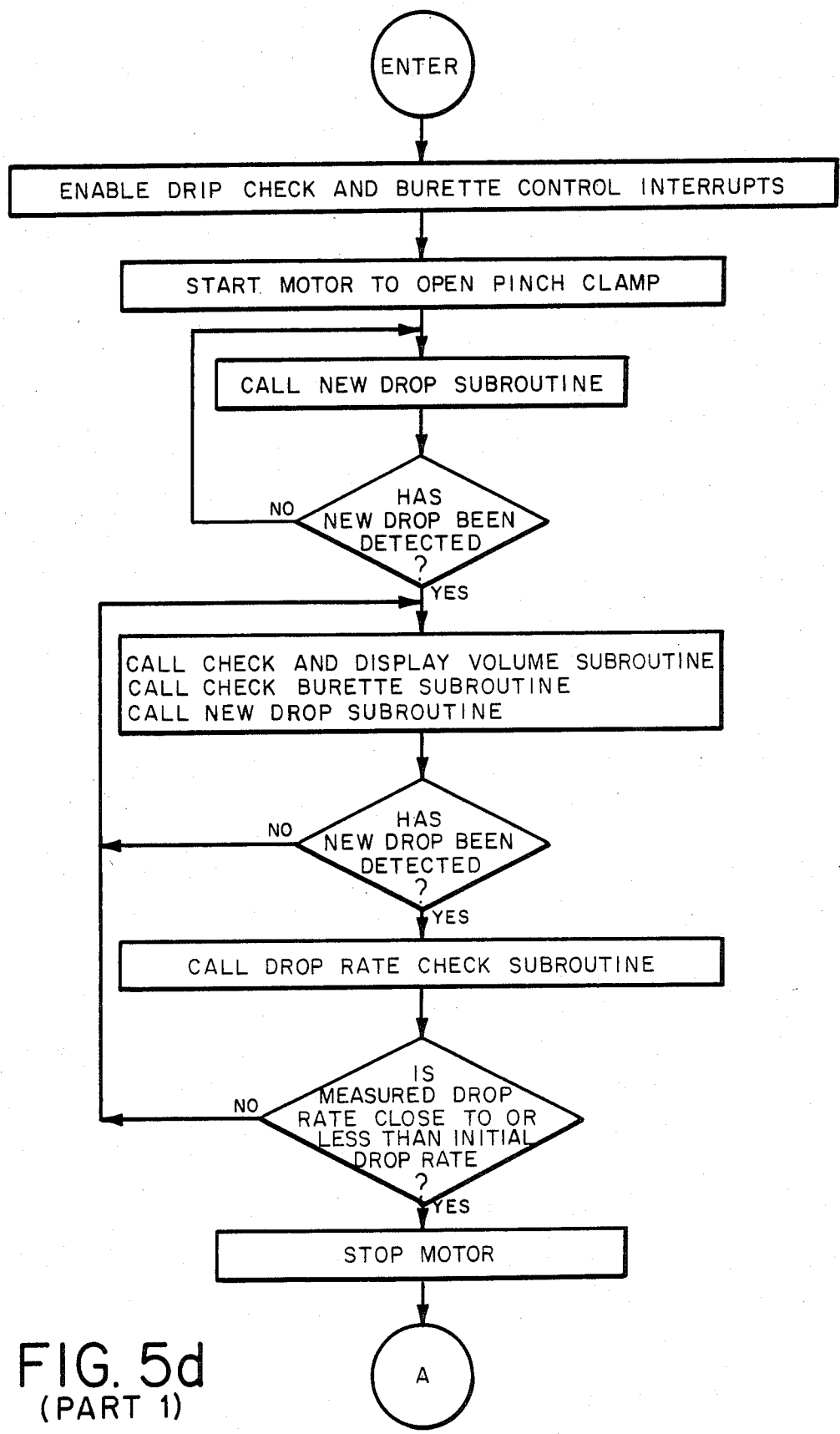
FIG. 5d (PART 1)

(PART 2)

INTRAVENOUS SET FLOW CONTROL DEVICE

BACKGROUND OF THE INVENTION

This invention relates to flow control devices for use with intravenous sets to control the rate at which fluids are passed from a container to a living subject.

A wide range of medications and nutrients are commonly administered intravenously. This is done by passing fluids containing the medication or the nutrient at a controlled rate via a needle or a cannula into a vein of a patient. Depending on the medication or nutrient being administered and the state of health of the patient, the flow rate at which fluids are infused may be critical. Furthermore, the total volume of fluid infused is typically also of interest.

In the past, two major approaches have been used to control the rate at which fluids are administered intravenously. The first approach is to use a conventional drip chamber which is manually controlled to adjust the drop rate through the drip chamber until the drops fall at a predetermined rate. This approach brings with it the advantage of simplicity in that only gravitational forces are needed to maintain the flow of fluids through the drip chamber.

However, manually controlled drip chambers are not satisfactory for all applications, for such drip chambers can permit fluid flow rate inaccuracies of as much as 30% above the requested flow rate or 60% below the requested flow rate. These inaccuracies are due to the fact that the size of individual drops passing through the drip chamber can vary as a function of the viscosity of the fluid being administered, the flow rate with which the fluid passes through the drip chamber, fluid pressure, and vibrational influences on the drip chamber. Furthermore, unless the drip chamber is carefully made to exacting tolerances, the drop volume may vary from one drip chamber to the next. This means that a drop rate appropriate for a preselected fluid flow rate with a first drip chamber is not necessarily appropriate for a second drip chamber, even if fluid viscosity and pressure are identical. Moreover, because of cold flow of tubing used in conjunction with conventional pinch clamps, a conventional, manually controlled drip chamber which is operating at a desired drop rate initially may well vary from this drop rate in time.

In an effort to provide greater accuracy of infusion rates, positive displacement infusion pumps have come into widespread use. Such pumps provide the advantage of accurately controlled infusion rates, largely independently of the pressure or the viscosity of the fluid being infused. However, such infusion pumps suffer from their own disadvantages. Because they typically operate at pressures of up to 60 psi, the danger of overpressure infusion is always present. Furthermore, infusion pumps tend to be relatively expensive, as well as heavy and cumbersome. In large part, the weight of infusion pumps is related to the size of the back up battery needed to power the pump in the event of a power failure. Because pumps operate motors on a regular basis, back up batteries for infusion pumps require large capacity. Furthermore, many infusion pumps bring with them problems related to the need to thread the IV set properly through the pump, and many infusion pumps require relatively expensive IV sets. Of course, when expensive IV sets are required for infusion pumps, it is less feasible to use the same intravenous set whether or not a pump is being used. This means that many hospitals are required to maintain stocks of two or more intravenous sets, and that a patient may well be subjected to the inconvenience of having an intravenous set replaced if the patient's physician determines that an infusion pump should be used.

SUMMARY OF THE INVENTION

The present invention is directed to an improved intravenous set controller which to large extent overcomes the disadvantages described above. This invention can be embodied in relatively small, compact, lightweight controllers which provide extremely accurate control over infusion rates, but which require relatively low-capacity batteries and are therefore materially less cumbersome than many infusion pumps. In addition, the preferred embodiments of the controller of this invention are quiet and reliable in operation as well as significantly less expensive than many infusion pumps. Furthermore, the controller of this invention can be used with intravenous sets which are not substantially more expensive than standard intravenous sets in common use. This allows a hospital to stock only a single intravenous set for use in both controlled and uncontrolled infusions. The controller of this invention does not actively pump fluids into the patient in order to obtain precise control over the rate of infusion, as does an infusion pump. Therefore, dangers related to overpressure infusion are entirely avoided with the controller of this invention. Furthermore, since the controller of this invention provides active monitoring and control of the infusion rate, the drop forming device on the intravenous set is no longer required to be manufactured to extremely close tolerances. This aspect of the invention further reduces the cost of intravenous sets which are usable with the controller of this invention.

According to this invention, a flow control device is provided for use with an intravenous set which comprises a drip chamber, a volumetric chamber having a preselected volume connected to the drip chamber, and externally actuated means for selectively interrupting fluid flow into the volumetric chamber. This fluid flow control device includes means for storing a selected flow rate, means for automatically controlling fluid flow out of the drip chamber to cause the measured drop rate in the drip chamber to approach a selected drop rate, means for automatically actuating the interrupting means to allow the volumetric chamber to fill and empty repeatedly, and means for automatically and repeatedly measuring the rate at which the volumetric chamber empties, and for automatically modifying the selected drop rate in response thereto to cause the actual flow rate of fluid out the drip chamber to approach the selected flow rate. Alternative embodiments can measure the rate at which the volumetric chamber empties either by measuring the time or the number of drops required for the volumetric chamber to empty.

Thus, the flow control device of this invention both (1) controls the flow rate through the intravenous set such that the drop rate approaches a selected drop rate, and (2) simultaneously adjusts the selected drop rate to accommodate the instantaneously prevailing drop size. If for any reason the drop size varies, as for example due to variations in the drop forming means included in the intravenous set or to variations in the pressure or viscosity of the fluid being infused, the fluid control device of this invention automatically detects this variation and corrects for it. An accurate rate of fluid delivery is maintained even in the face of varying drop size, varying fluid pressure, varying fluid viscosity, and the like.

The control device of this invention brings with it all of the advantages of a gravity powered infusion system. There is no danger of supplying fluid at excessive pressure to the patient, and the size, weight, and battery requirements of positive displacement pumps are avoided. Thus, the present invention provides significantly improved control over the flow rate with which fluids are administered without suffering from the important disadvantages of infusion pumps discussed above. The controller of this invention can also readily include alarms which provide a separate indication for occlusion of the intravenous set, excessive flow rates (such as those associated with an open line), and air in the intravenous set.

The invention itself, together with further objects and attendant advantages, will best be understood by reference to the following detailed description taken in conjunction with the accompanying drawings.

BRIEF DESCRIPTION OF THE DRAWINGS

FIG. 2b is a schematic view corresponding to FIG. 2a.

FIGS. 4a, 4b and 4c are schematic views of alternate embodiments of the means for actuating the upper valve.

DETAILED DESCRIPTION OF THE PRESENTLY PREFERRED EMBODIMENTS

Figure 1:
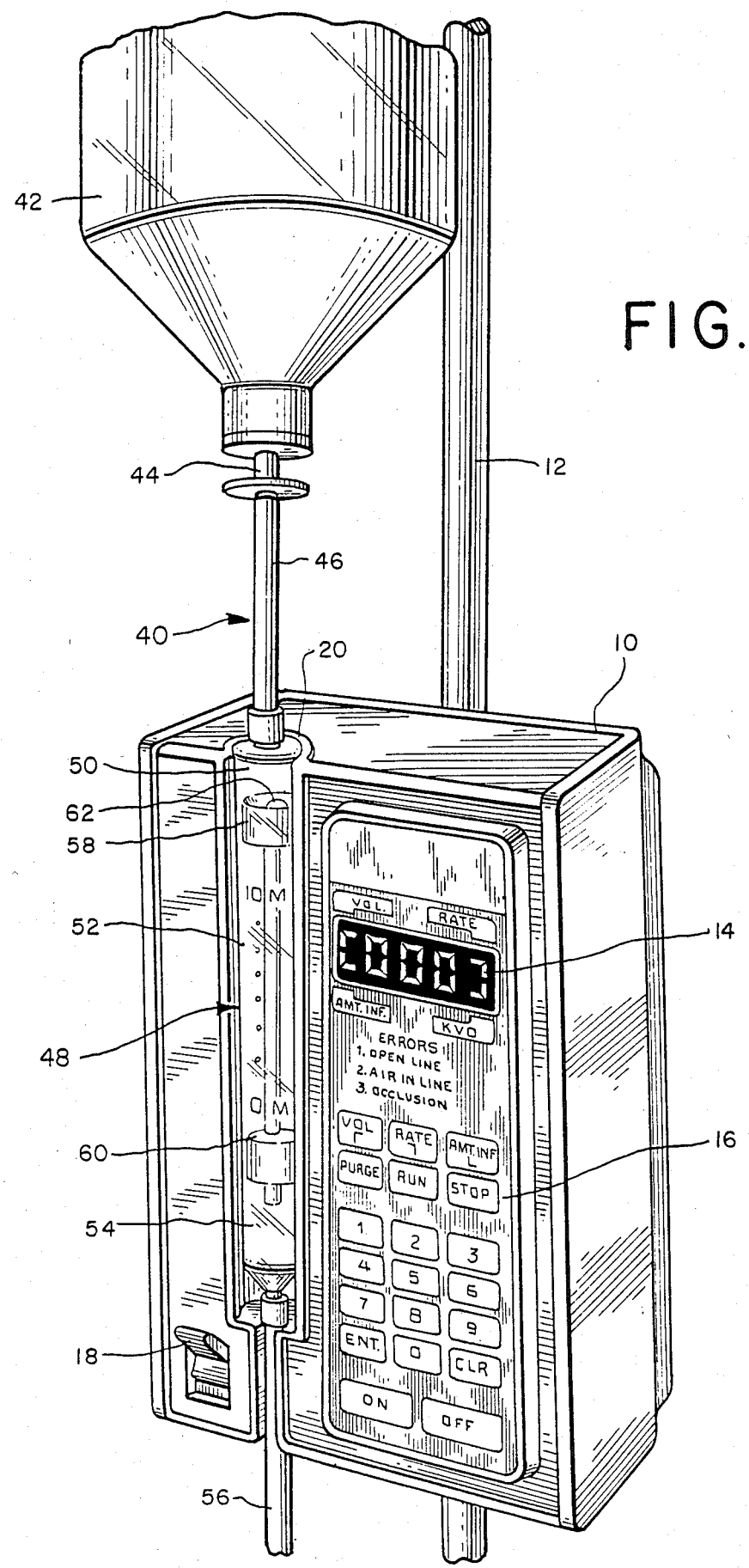
FIG. 1 is a perspective view of a presently preferred embodiment of the flow control device of this invention in which an intravenous set has been installed.

Turning now to the drawings, FIG. 1 shows a perspective view of a controller 10 which incorporates a presently preferred embodiment of this invention. As shown in FIG. 1, this controller 10 is mounted on a vertically upright pole 12. The controller 10 includes a digital display 14 and a keyboard 16. The function and operation of the display 14 and the keyboard 16 will be explained below in detail in conjunction with the flow charts which form part of this specification.

The controller 10 also includes a manually operated pinch clamp lever 18 and a receiving well 20. The receiving well 20 is sized to receive and retain in place a portion of an IV set 40. As shown in FIG. 1, this IV set 40 is provided with connecting means 44 for connecting the IV set 40 to a container 42. In practice, the container 42 would contain fluids containing a nutrient or a medication to be infused intravenously into a patient.

The IV set 40 also includes an upper tube 46 which extends between the connecting means 44 and a housing 48. The housing 48 is sized to fit within the receiving well 20 such that the housing 48 can be inserted from above into the receiving well 20, but is then prevented from moving horizontally out of the receiving well 20. The housing 48 defines three separate chambers within it: an upper valve chamber 50, an intermediate volumetric chamber 52, and a lower drip chamber 54. The lowermost portion of the housing 48 is coupled to a lower tube 56 which extends to means for connecting the lower tube 56 to an insertion device such as a needle or cannula adapted to introduce fluids into the patient.

The three chambers defined by the housing 48 are separated by means of an upper barrier 58 and a lower barrier 60. The three chambers 50, 52, 54 defined by the housing 48 are arranged in series such that fluid flows from the container 42 via the upper tube 46 down through the valve chamber 50, the volumetric chamber 52, and the drip chamber 54 to the lower tube 56.

Figure 2A:
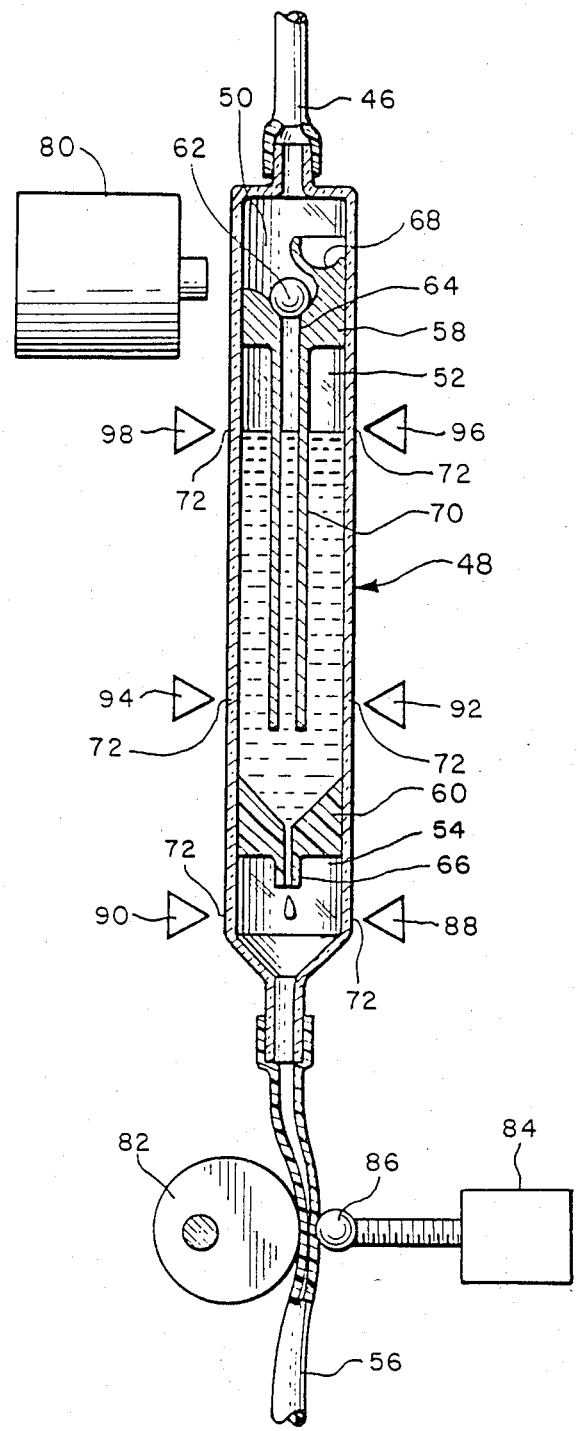
FIG. 2a is a schematic view of portions of the embodiment of FIG. 1.
Figure 2B:
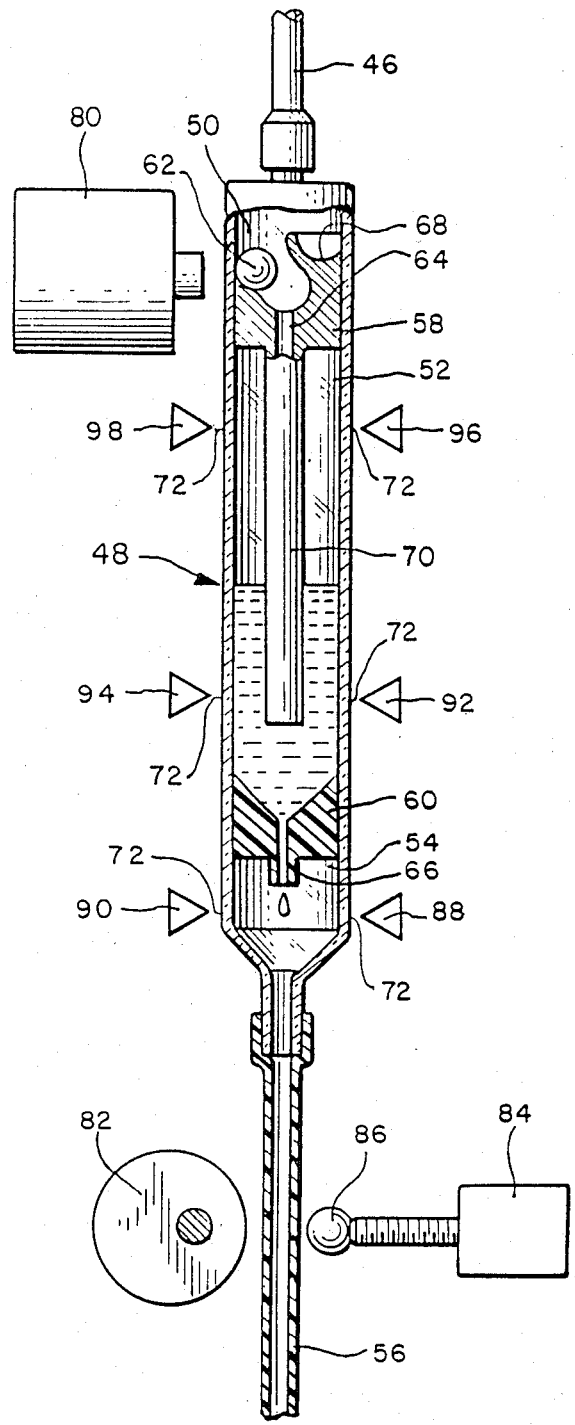

FIGS. 2a and 2b show a more schematic view of portions of the controller 10 and the IV set 40. As shown in FIGS. 2a and 2b, the upper barrier 58 of the housing 48 defines a valve seat 64 which extends between the valve chamber 50 and the volumetric chamber 52. A valve member such as a magnetically responsive ball 62 is included inside the valve chamber 50. The ball 62 is sized and adapted to position itself against the valve seat 64 in the absence of magentic forces, and thereby to interrupt fluid flow from the valve chamber 50 into the volumetric chamber 52.

A pocket 68 is defined in an interior surface of the valve chamber 50. This pocket 68 is provided to retain the ball 62 away from the valve seat 64 when desired. By suitably manipulating the housing 48, the ball 62 can either be positioned inside the pocket 68 (in which case the valve seat 64 provides a continuously open fluid passageway between the valve chamber 50 and the volumetric chamber 52), or the ball 62 can be allowed to assume the position shown in FIG. 2a (in which case the ball 62 seals against the valve seat 64 in the absence of magnetic forces). In alternate embodiments of the IV set 40, a cap magnet can be positioned on the exterior of the housing 48 to hold the ball 62 away from the valve seat 64 when desired.

The lower barrier 60 which separates the volumetric chamber 52 from the drip chamber 54 is provided with a drip forming device 66 at its lower end. Thus, the lower barrier 60 provides a fluid passageway which is constantly open between the volumetric chamber 52 and the drip chamber 54, and fluids passing into the drip chamber 54 are formed into individual drops by means of the drip forming device 66.

The volumetric chamber 52 is carefully sized such that the volume of the volumetric chamber 52 between two predefined levels is equal to a predetermined quantity, 10 milliliters in this example. A conduit 70 is provided which extends downwardly from the valve seat 64 to a point below the lower of these two levels. This conduit 70 serves to confine fluids entering the volumetric chamber 52 to a predetermined portion of the volumetric chamber 52 until such fluids reach a point below the lower level. As used herein, the term "volumetric chamber" is used in its broad sense to cover chambers which are defined in part by detector levels rather than physical walls. Thus, the volumetric chamber 52 is described as empty when the fluid level reaches the lower level and full when it reaches the upper level.

With respect to materials, the upper end lower tubes 46, 56 of this embodiment are formed of PVC materials. Thus, the tubes 46, 56 are flexible and collapsible. The housing 48 and the upper and lower barriers 58,60 are formed of acetate, such that they are substantially rigid, dimensionally stable, and transparent. The transparency of the housing 48 is important in this embodiment, for the controller 10 photoelectrically senses fluid level and detects drops within the housing 48. Thus, the portions of the housing 48 adjacent the photosensors and light sources included in the controller 10 in effect act as windows 72 which pass optical signals through the housing 48. As used herein, the term "window" is used in its broad sense to include transparent and translucent regions of a housing, whether or not such regions are distinguished in any way from remaining portions of the housing.

FIGS. 2a and 2b also provide schematic representation of certain portions of the controller 10. As shown in FIG. 2a, the controller 10 includes an electromagnet 80 which is positioned adjacent the valve chamber 50. When the electromagnet 80 is energized the ball 62 is moved from the position shown in FIG. 2a to that shown in FIG. 2b, thereby allowing fluids to pass from the valve chamber 50 to the volumetric chamber 52.

The controller 10 also includes a user positioned pinch clamp jaw 82, the position of which is controlled by means of the pinch clamp lever 18. The jaw 82 is movable between an open position in which the lower tube 56 can freely be inserted in the controller 10, and a closed position in which the controller 10 is capable of controlling fluid flow through the lower tube 56. In the drawings, FIG. 2a schematically shows the closed position of the jaw 82 and FIG. 2b schematically shows the open position of the jaw 82. A motor 84 is provided which serves to control the position of a pinch clamp jaw 86. This jaw 86 is positioned to oppose the jaw 82, such that when the jaw 82 is in the closed position shown in FIG. 2a, the flow rate through the lower tube 56 can be controlled by means of the motor 84 and the jaw 86. In this preferred embodiment, the jaw 86 is an eccentric disc having a diameter of about two inches which rotates about an axis which is about ¼ inch eccentric. A gear reduction of about 1740:1 between the motor 84 and the jaw 86 provides a jaw rotation rate of about 1 or 2 RPM. Because of this gear reduction, the jaw 86 remains immobile after the motor 84 is de-energized.

As shown in FIGS. 2a and 2b, three light sources 88, 92, 96, are positioned adjacent the housing 48 at three preselected levels. Similarly, three photosensors 90, 94, 98 are positioned in the controller 10 such that each is aligned with a respective one of the light sources 88, 92, 96. The light source 88 and the photosensor 90 cooperate to form a drop detector; the signal generated by the photosensor 90 serves as an indication of the passage of drops formed by the drop forming device 66. The light source 92 and the photosensor 94 cooperate to form a lower level fluid detector. The signal generated by the photosensor 94 varies as a function of whether the fluid level within the volumetric chamber 52 is above or below the lower level defined by the level of the photosensor 94. Similarly, the light source 96 and the photosensor 98 cooperate to form an upper level fluid detector which detects whether the fluid level in the volumetric chamber 52 is above or below the upper level defined by the photosensor 98. The conduit 70 extends within the volumetric chamber 52 to a point below the lower level light source and photosensor 92, 94. In this way, fluid entering the volumetric chamber 52 is confined to a portion of the volumetric chamber 52 which is separated from the portion of the volumetric chamber 52 viewed by the upper and lower photosensors 94, 98. Erroneous signals related to the downward flow of fluid into the volumetric chamber 52 are thereby avoided.

Figure 3:
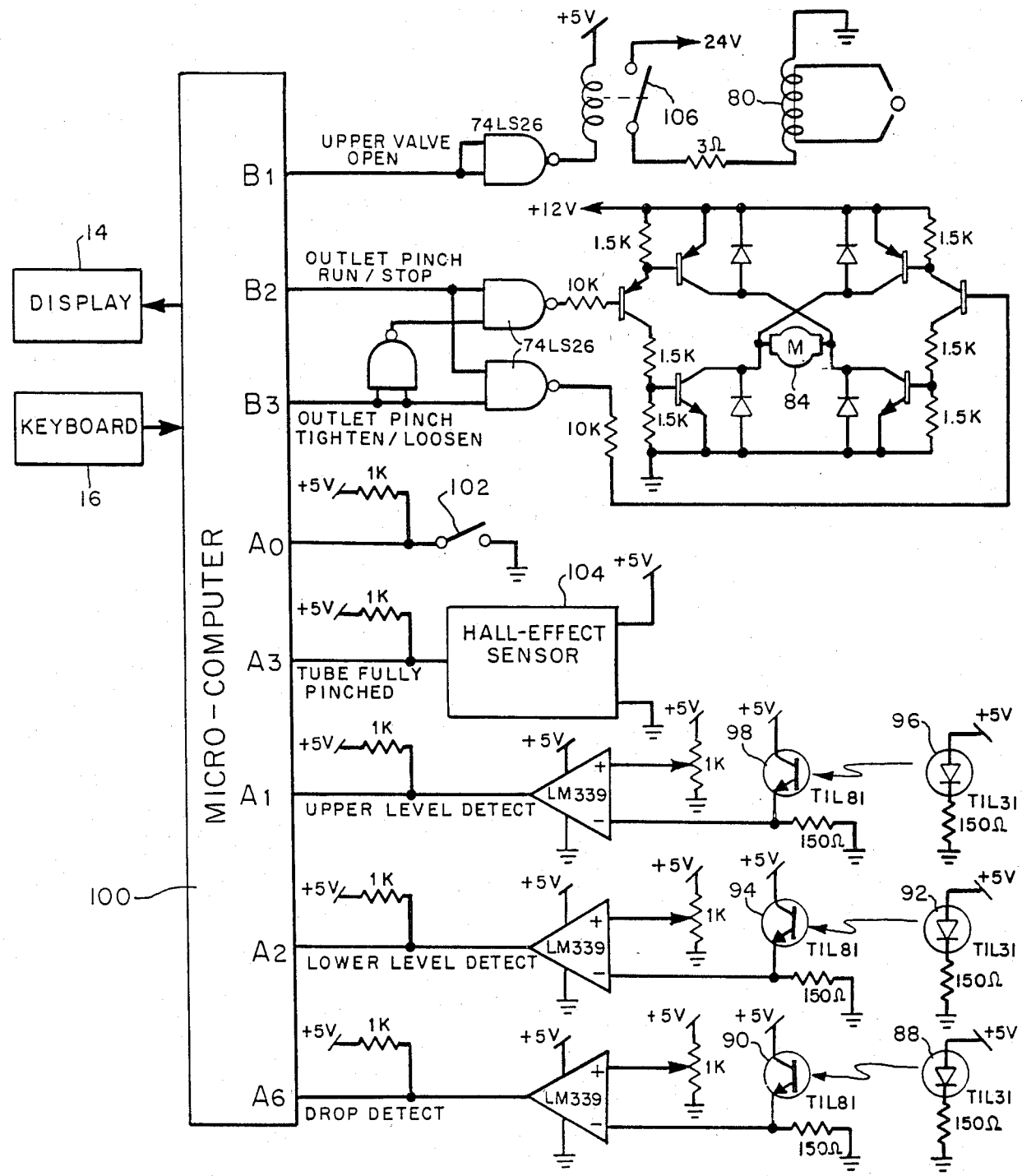
FIG. 3 is an electrical schematic diagram of the controller of FIG. 1.

FIG. 3 shows an electrical schematic of the controller 10. As shown in FIG. 3, the controller 10 includes a microcomputer 100 which is coupled to the display 14 and the keyboard 16. The microcomputer receives inputs from the three photosensors 90, 94, 98. In addition, the microcomputer 100 receives an input signal from a Hall effect sensor 104. This sensor 104 is positioned to respond to the magnetic field of a magnet (not shown) which is mounted on the motor positioned pinch clamp jaw 86. When the jaw 86 is positioned to the fully clamped position, the sensor 104 generates a signal which is applied to the computer 100 as an indication that the jaw 86 has reached the fully pinched position. A fifth input signal to the computer 100 is provided which allows the computer 100 to determine the position of the user positioned pinch clamp jaw 82. This input signal is provided by a switch 102 which changes state depending on whether the user position pinch clamp jaw 82 is positioned in the open position shown in FIG. 2b or the closed position shown in FIG. 2a.

The computer 100 is also provided with three digital outputs. The first output controls a relay 106 which in turn controls the flow of current through the electromagnet 80. In this preferred embodiment, the electromagnet 80 is formed of 2500 turns of number 26 wire on a ⅜ inch bobbin having a core. Thus, the first output allows the controller 10 to open or to close the valve included in the valve chamber 50 as desired.

The second and third computer outputs are used to control the operation of the motor 84. One of these two outputs determines whether the motor 84 is running or stopped, and the other output determines the direction of the motor (i.e. whether the motor is tightening the motor positioned pinch clamp jaw 86 against the lower tube 56 or loosening the jaw 86).

The details of the input and output circuits for the computer 100 are shown in FIG. 3, in which light emitting diodes, phototransistors, amplifiers, and logical gates are identified by industry standard part numbers and resistors are identified by resistance in ohms. The relay 106 of this preferred embodiment is distributed by the Elec-trol Company under Part No. BBS 1A05A10. The Hall effect sensor 104 of this embodiment is distributed by the Archer Company as Part No. 276-1646. The display 14 is a standard five-digit, seven-segment display in which the leftmost and rightmost digits are used as indicators rather than as numerical displays. The keyboard 16 can be formed in any conventional manner, and does not per se form part of this invention.

Before proceeding to a detailed description of the operation of the controller 10, it should be pointed out that the present controller can be adapted for use with a wide range of upper valves in the IV set 40. Three alternate configurations are shown in FIGS. 4a, 4b and 4c.

As shown in FIG. 4a, one alternative approach is to eliminate the valve chamber 50 entirely from the IV set 40 and to substitute a pinch clamp in the controller 10 made up of a fixed pinch clamp jaw 152 and a motor driven pinch clamp jaw 154. These jaws 152, 154 bear against a flexible, resilient tube 150 which can for example be formed by the upper tube 46 interconnecting the housing 48 with the connecting means 44. In this alternate embodiment, it is the tube 150 which forms the means for interrupting fluid flow into the volumetric chamber 52, and this means is actuated by the jaws 152, 154.

In another alternative embodiment shown in FIG. 4b, the ball 62 is replaced with a tiltable element 160 which defines a longitudinal axis extending parallel to the length of the housing 48. This tiltable element 160 is formed of a magnetically responsive material, and it is provided with a valve portion 164 which seals against a valve seat 166. A spring 162 is provided which biases the tiltable element 160 into a sealing position, as shown in FIG. 4b. By applying magnetic forces with an electromagnet similar to the one described above in conjunction with FIGS. 1 through 3, the tiltable element 160 may be tilted to one side, thereby allowing fluid to flow downwardly through the valve seat 166 into the volumetric chamber 152. In some applications such a tilt valve may require smaller currents in the electromagnet 80 than does the ball valve of FIGS. 1, 2a, and 2b.

Yet another alternative is shown in FIG. 4c, in which an inlet tube 170 and an outlet tube 172 are coupled to a diaphragm valve 174. This diaphragm valve 174 includes a diaphragm 176. An externally situated platen 178 is provided. This platen 178 can be used to push the diaphragm 176 against the tubes 170, 172 in order to interrupt fluid flow through the diaphragm valve 174. The lower end of the outlet tube 172 is connected to pass fluid into the volumetric chamber 52.

From the foregoing discussion of FIGS. 4a, 4b and 4c, it should be apparent that a wide range of valves can be used in conjunction with the controller of this invention. In each case, the valve should be capable of remote actuation without destroying the integrity of the IV set, and without allowing foreign materials to enter the IV set.

Turning now to the flow charts of FIGS. 5a through 5k, the program of the microcomputer 100 will be described. A complete assembly language listing for the presently preferred embodiment of this program is included in the attached Appendix A. That listing forms the fundamental disclosure of the program for the computer 100. The attached flow charts and the following discussion have been provided to clarify the disclosure of the listing. Table 1 provides a cross reference between the listing and the flow charts of FIGS. 5a–5k.

TABLE 1

| Figure No. | Identifying Name of Start of Corresponding Portion of Listing of Appendix A |
| --- | --- |
| 5a | POWER UP |
| 5b | PURGE |
| 5c | SETUP LOOP |
| 5d | START FLOW |
| 5e | CHK NEW DROP |
| 5f | MAIN LOOP |
| 5g | CHK BURETTE |
| 5h | DRIP TIME CHK |
| 5i | ADJUST RATE |
| 5j | ERROR REPORT |
| 5k | TIMER INT |

The attached listing is suitable for use in an AIM 65 microcomputer marketed by Rockwell. It will be appreciated however that alternate embodiments of this invention may well use other microcomputers more suitable for compact packaging. In this case, it is a straightforward matter to convert the program disclosed in the attached Appendix, flow charts, and description into a form suitable for such alternate computer.

Figure 5A:
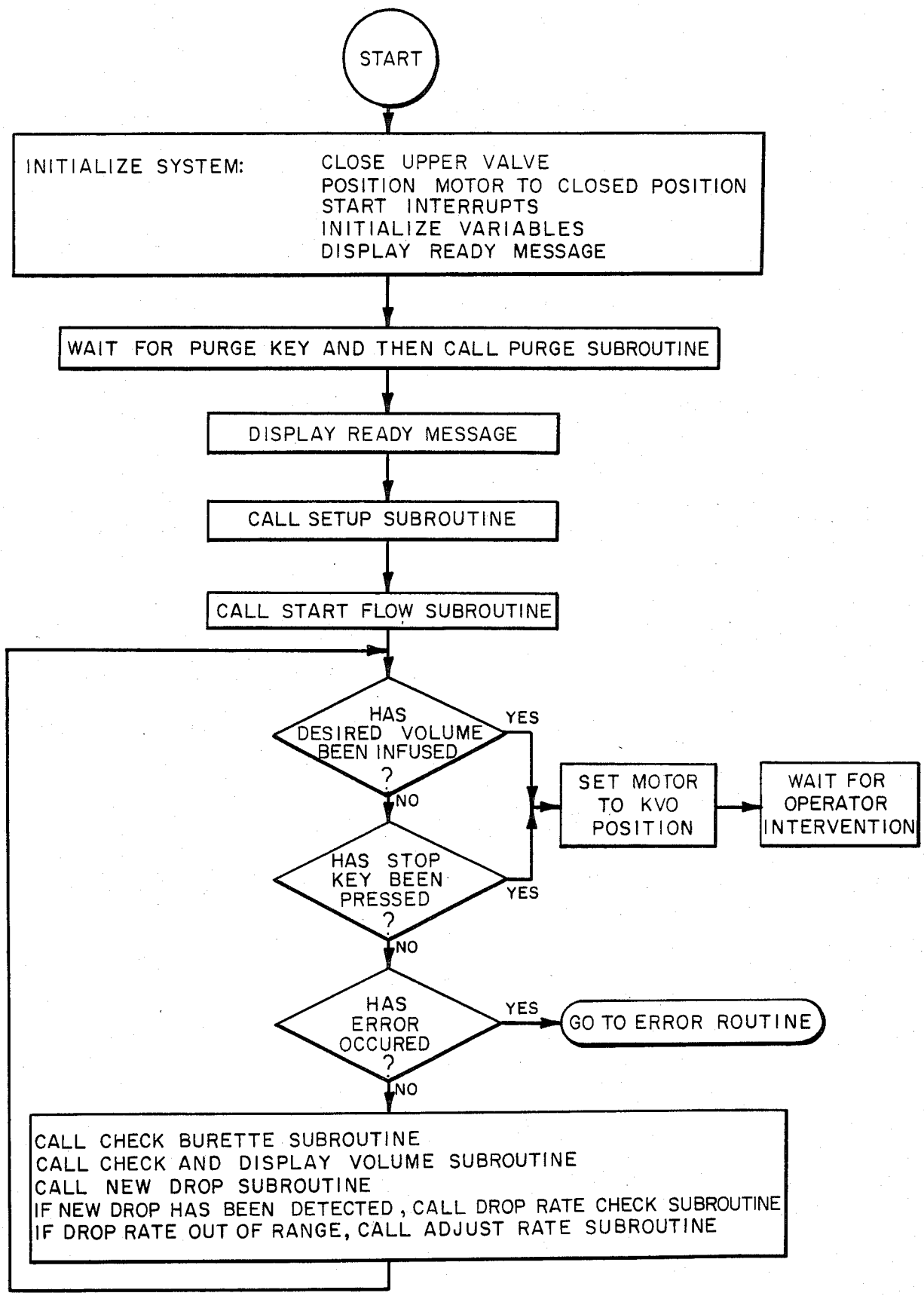
FIGS. 5a through 5k are flow charts of the program of the preferred embodiment of FIG. 1.

FIG. 5a shows the Main Control Sequence for the program of the computer 100. When power is applied to the computer 100, the computer 100 first initializes the controller 10. This is done by de-energizing the electromagnet 80, positioning the motor 84 to the fully pinched position, starting the program interrupts, initializing program variables, and displaying a ready message on the display 14. The program then waits for the operator to depress the Purge key included in the keyboard 16.

Figure 5B:
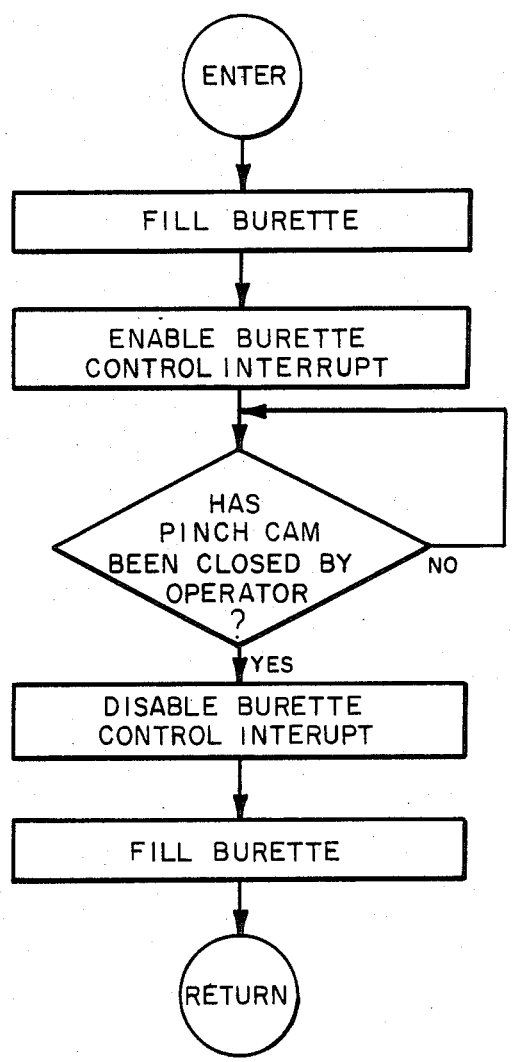

Once the Purge key is pressed, the Purge Subroutine shown in FIG. 5b is executed. This subroutine operates to fill the volumetric chamber 52 to the level of the upper photosensor 90 and to enable the burette control interrupt. In the following discussion, the term "burette" will on occasion be used to refer to the volumetric chamber 52. When the burette control interrupt is enabled, the interrupt service routine shown in FIG. 5k operates to fill the burette automatically when the burette is empty and to deenergize the electromagnet 80 when the burette is full. At this point, the controller 10 does not control fluid flow through the drip chamber 52. Rather, the controller 10 allows the user to cause an indefinite amount of fluid to be passed through the drip chamber 52. This mode of operation is provided to allow the user to purge the IV set 40 by passing fluids through the IV set 40 to remove air from the system.

Once the user is satisfied that the IV set 40 has been properly purged, the user closes the pinch clamp lever 18. The Purge Subroutine of FIG. 5b responds to the closing of the pinch clamp lever 18 by disabling the burette control interrupt and then filling the burette to the upper level.

Figure 5C:
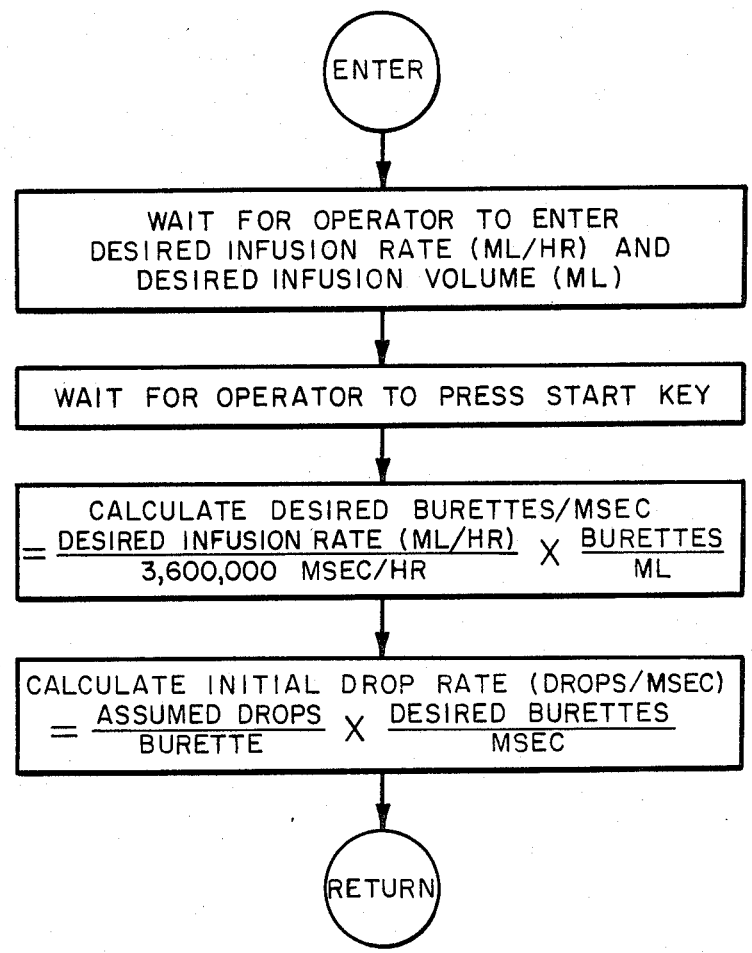

At this point, the program of FIG. 5a displays a ready message and then calls the Set Up Subroutine shown in FIG. 5c. This subroutine waits for the user to enter the desired infusion rate (measured in units of milliliters per hour) and the desired total infusion volume (measured in milliliters). Once these two parameters have been entered and the user has pressed the Start key, the Set Up Subroutine of FIG. 5c calculates two values. First, the desired burettes per millisecond parameter is calculated by converting the desired infusion rate into the units of milliliters per millisecond and then by multiplying this quantity by a parameter having the units burettes per milliliter. In this preferred embodiment, the volumetric chamber 52 defines a volume between the upper and lower levels of 10 milliliters, and thus this parameter has the value 0.10. The program then calculates an initial drop rate (drops per millisecond). The initial drop rate is calculated as the product of a stored parameter (the assumed drops per burette) and the previously calculated parameter desired burettes per millisecond. Once these two quantities have been calculated and stored, the Set Up Subroutine of FIG. 5c returns control to the Main Control Sequence of FIG. 5a.

Figure 5D:
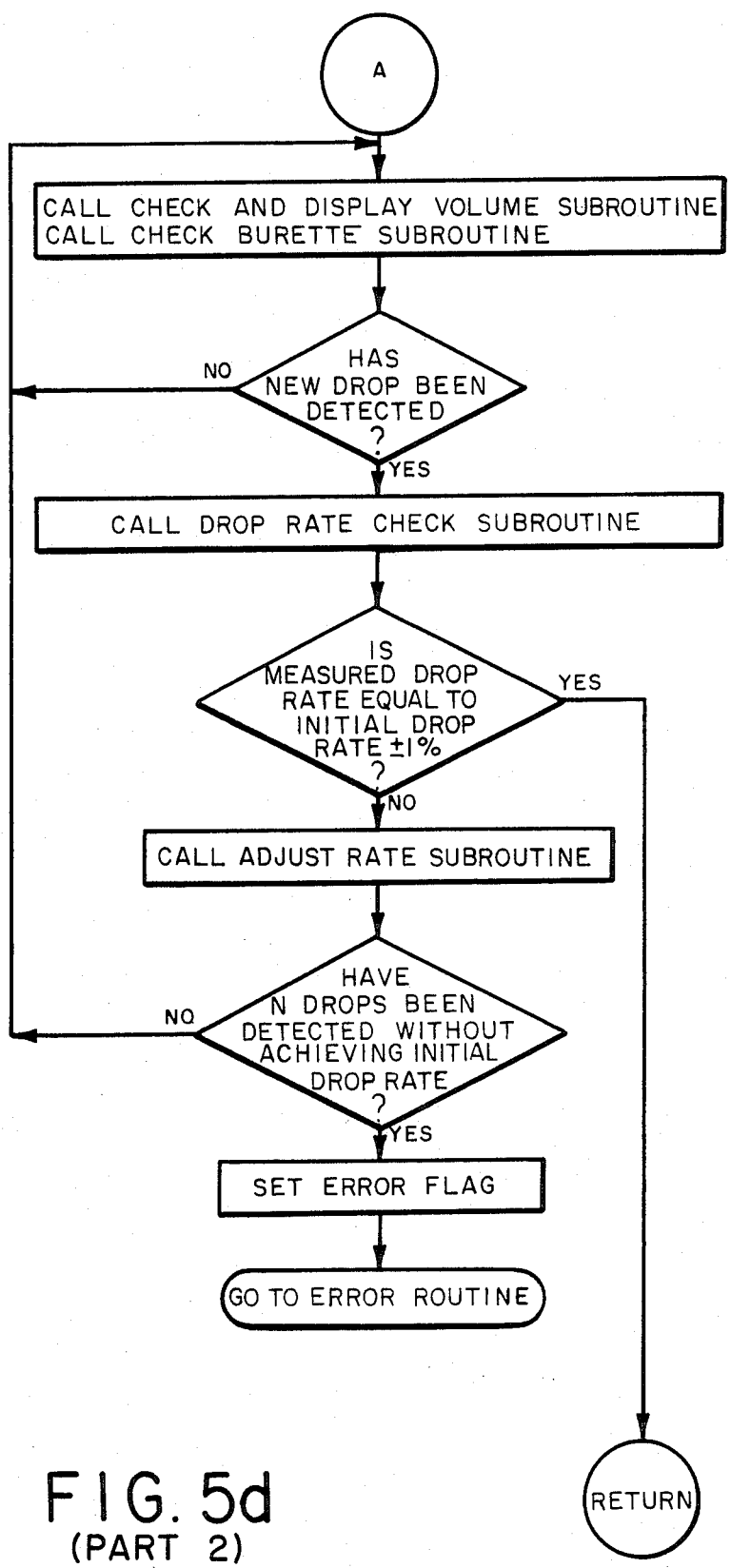

Next, the Start Flow Subroutine of FIG. 5d is executed. Generally speaking, this subroutine operates to control the motor 84 to adjust the position of the motor positioned pinch clamp jaw 86 such that the actual, measured drop rate (which is sensed by means of the light source 88 in the photosensor 90) is set equal to the just calculated initial drop rate. Once this condition is obtained, the motor 84 stopped and control is returned to the Main Control Sequence of FIG. 5a. In the event a predetermined number of drops fall before the actual drop rate is made to equal the initial drop rate, the subroutine of FIG. 5d sets an error flag and then calls an error routine flow charted in FIG. 5i. Thus, the Start Flow Subroutine of FIG. 5d sets the drop rate at a value which is determined as a function of stored parameters to produce approximately the desired infusion flow rate.

The Main Control Sequence of FIG. 5a then checks to determine if the desired volume has been infused or if the Stop key has been pressed by the user. If either of these conditions is found to obtain, the motor 84 is moved to a predetermined position (the Keep Vein Open or KVO position) to reduce the flow rate of fluid through the drip chamber 54 to a very low rate, sufficient to prevent the IV set 40 from clogging. The program then waits for intervention by the user.

Assuming the Stop key has not been pressed, the desired volume has not been infused, and no errors have been detected, the program then enters a flow rate adjustment mode which operates to adjust the drip rate repeatedly in order repeatedly to improve the accuracy with which the actual rate of fluid flow through the IV set 40 approximates the desired infusion rate. This loop includes a number of separate subroutines, as shown in FIGS. 5e through 5j.

Figure 5E:
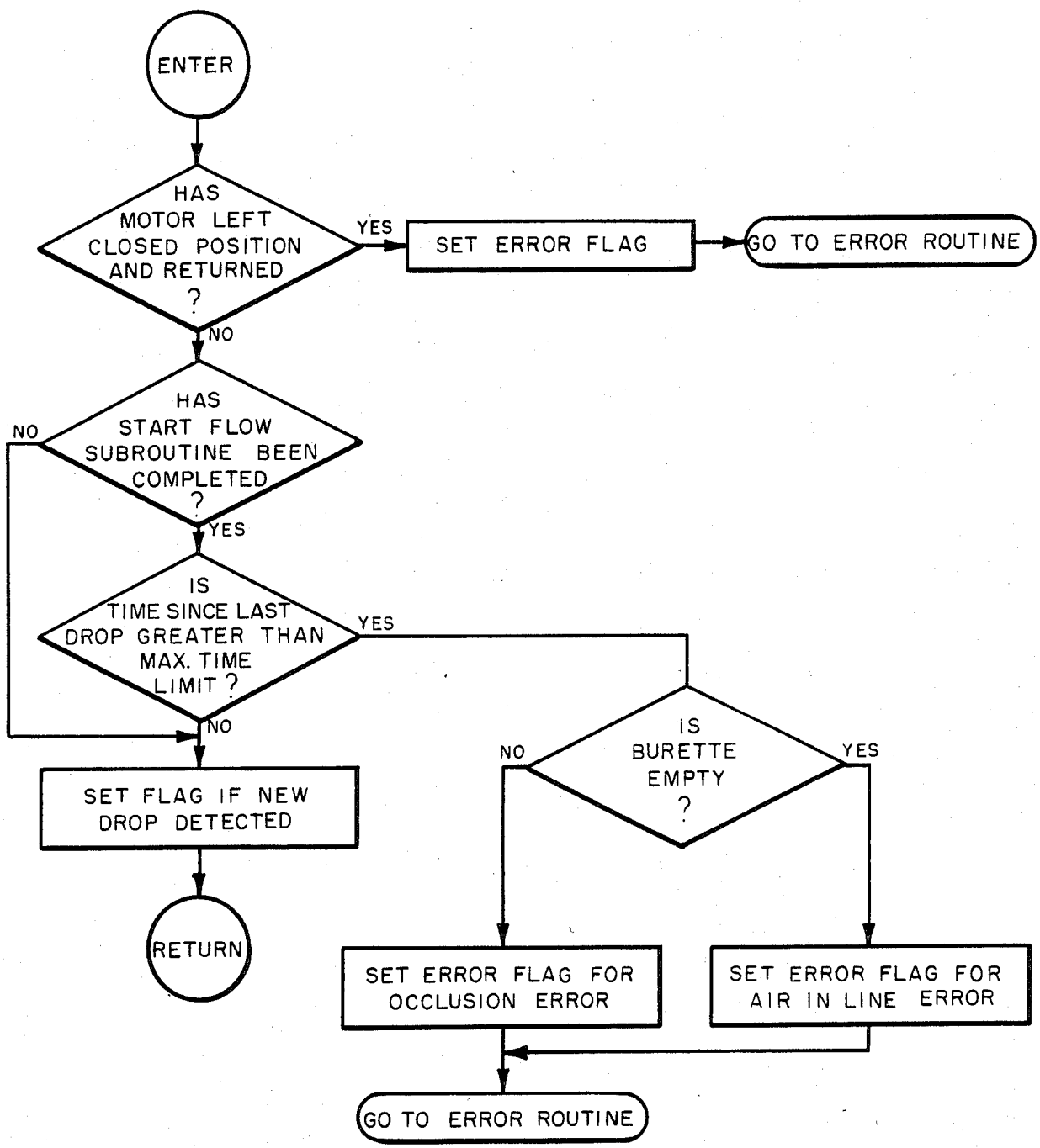
Figure 5F:
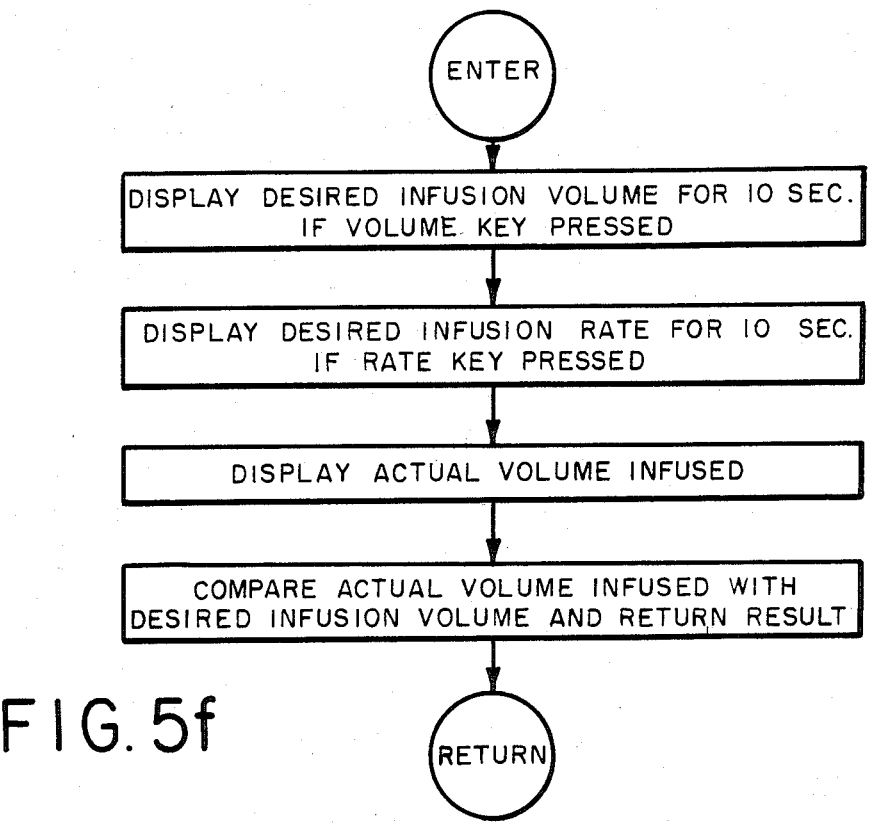

The Check and Display Volume Subroutine of FIG. 5f operates to control the display 14 in accordance with user requests. If the Volume key is pressed, the desired infusion volume is displayed for 10 seconds. If the Rate key is pressed, the desired infusion rate is displayed for 10 seconds. Otherwise, the actual volume infused is displayed. The subroutine also acts to compare the actual volume infused with the desired infusion volume and to return this result.

Figure 5G:
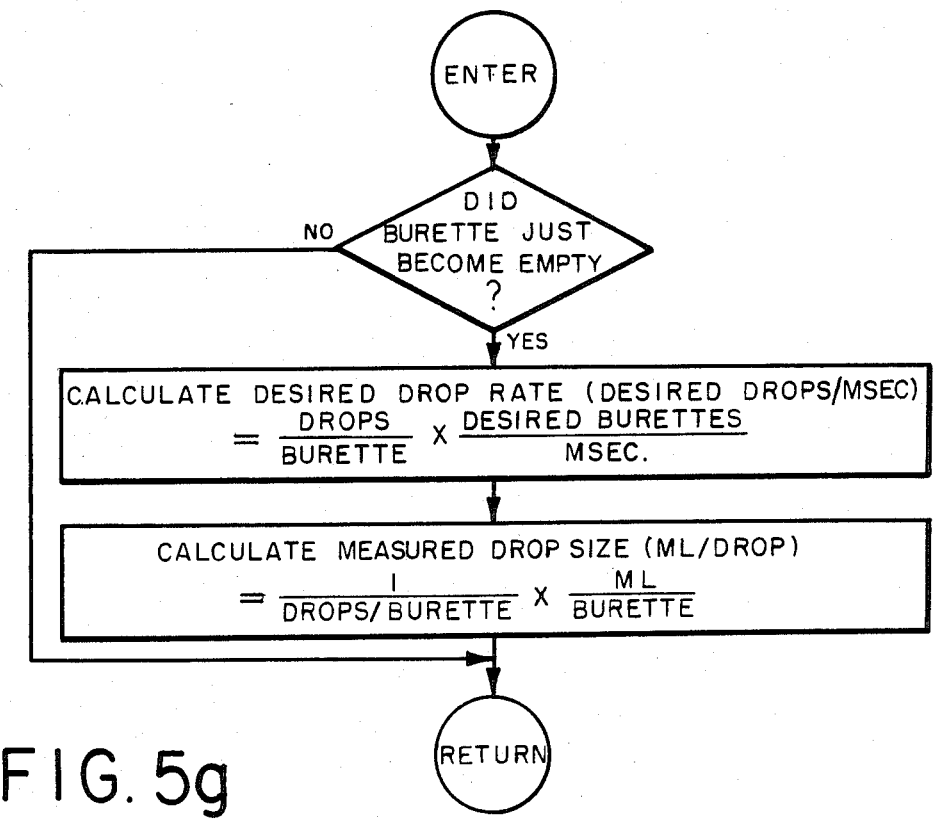

The subroutine of FIG. 5g is the Check Burette Subroutine. This subroutine first checks to determine if the burette just became empty, as indicated by the signal generated by the lower level photosensor 94. The routine simply returns without taking any action if the burette has not just become empty. However, if the burette has just become empty, the routine calculates the desired drop rate, a variable having the units of desired drops per millisecond. The desired drop rate is calculated as the product of the measured number of drops in the last burette times the desired burettes per millisecond. By counting the number of drops in each burette, the program in effect measures the actual volume of average drops of the burette and then uses this measured volume to adjust the desired drop rate. The first burette is infused using a stored estimate of the number of drops per burette. However, all subsequent burettes are infused at a drop rate which is determined as a function of the actual number of drops counted in the most recently infused burette. In this way, corrections are quickly made for variations in drop size due to changes in viscosity, pressure, or infusion rate. The Check Burette Subroutine of FIG. 5g also calculates the measured drop size by obtaining the product of the inverse of the total number of drops per burette multiplied by the known number of milliliters per burette.

FIG. 5e flowcharts the New Drop Subroutine. This subroutine first checks to determine whether the motor 84 has left the closed position and returned. If so, an appropriate error flag is set and the error routine is called. Otherwise, the program operates to check the time since the last drop against a maximum time limit. If the measured time is greater than the maximum time limit (indicating an excessively slow drop rate) the subroutine then determines whether or not the burette is empty (as indicated by the lower level photosensor 94). If the burette is empty, the program sets an error flag to indicate air in the line and calls the error routine. If the burette is not empty, indicating no lack of fluid supply to the burette, the New Drop Subroutine then sets the error flag to indicate an occlusion error and calls the error routine. In the event that the time since the last drop is not greater than the maximum time limit, the routine sets a flag if a new drop has been detected and then returns.

Figure 5H:
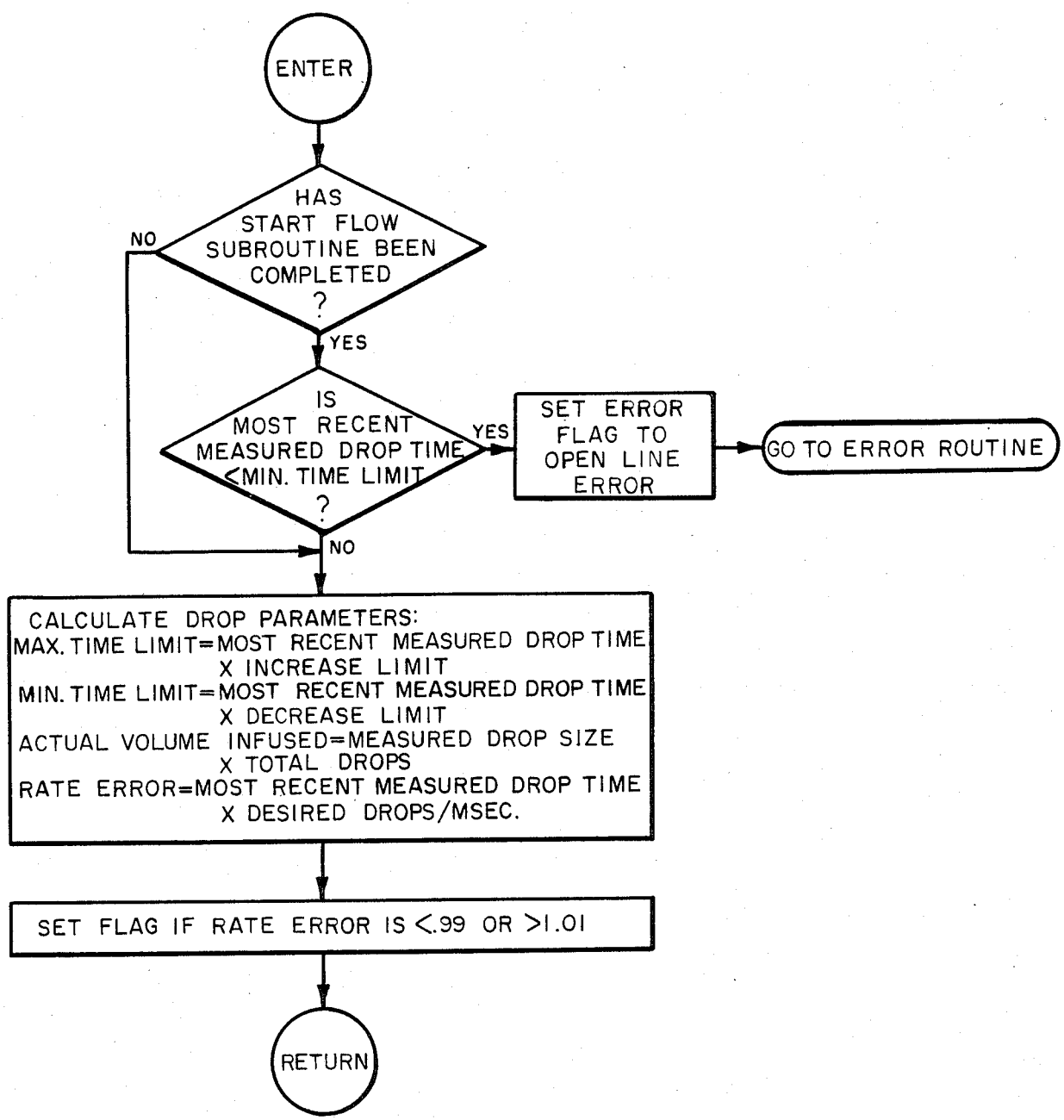

After each drop is detected, the Drop Rate Check Subroutine of FIG. 5h is executed. This subroutine first checks to determine if the most recently measured drop time is less than a minimum drop time limit. If so, the error flag is set to indicate an open line error, and the error routine is called. Otherwise, the subroutine calculates a number of parameters. First, it sets the maximum time limit equal to the most recently measured drop time times an increase limit (1.30 in this embodiment). The minimum time limit is then set equal to the most recently measured drop time times a decrease limit (0.80 in this embodiment). In this way, both the maximum and minimum time limits are allowed to track the actually measured drop time, as long as the actually measured drop time does not vary too abruptly. If it does, this abrupt change in the measured drop time is used as explained above as an indication of either an open line, an occlusion, or air in the line. In some applications, it may be desireable to enlarge the range of acceptacle drop times for the period just before the electromagnetic is activated and just after it is deactivated in order to reduce false alarms.

This subroutine also calculates the actual volume infused, which is equal to the measured drop size as determined in the Check Burette Subroutine multiplied by the total number of drops infused. Finally, the Drop Check Subroutine calculates the rate error which is equal to the most recently measured drop time multiplied by the desired drops per millisecond as determined in the Check Burette Subroutine. The rate error is equal to 1 in the event the most recently measured drop time corresponds to an instantaneous drop rate equal to the desired drop rate. The subroutine of FIG. 5a sets a flag if the rate error is less than 0.99 (indicating that the instantaneously prevailing drop rate is less than the desired drop rate) or if the rate error is greater than 1.01 (indicating that the instantaneously prevailing drop rate is greater than the desired drop rate). The Drop Rate Check Subroutine then returns.

Figure 5I:
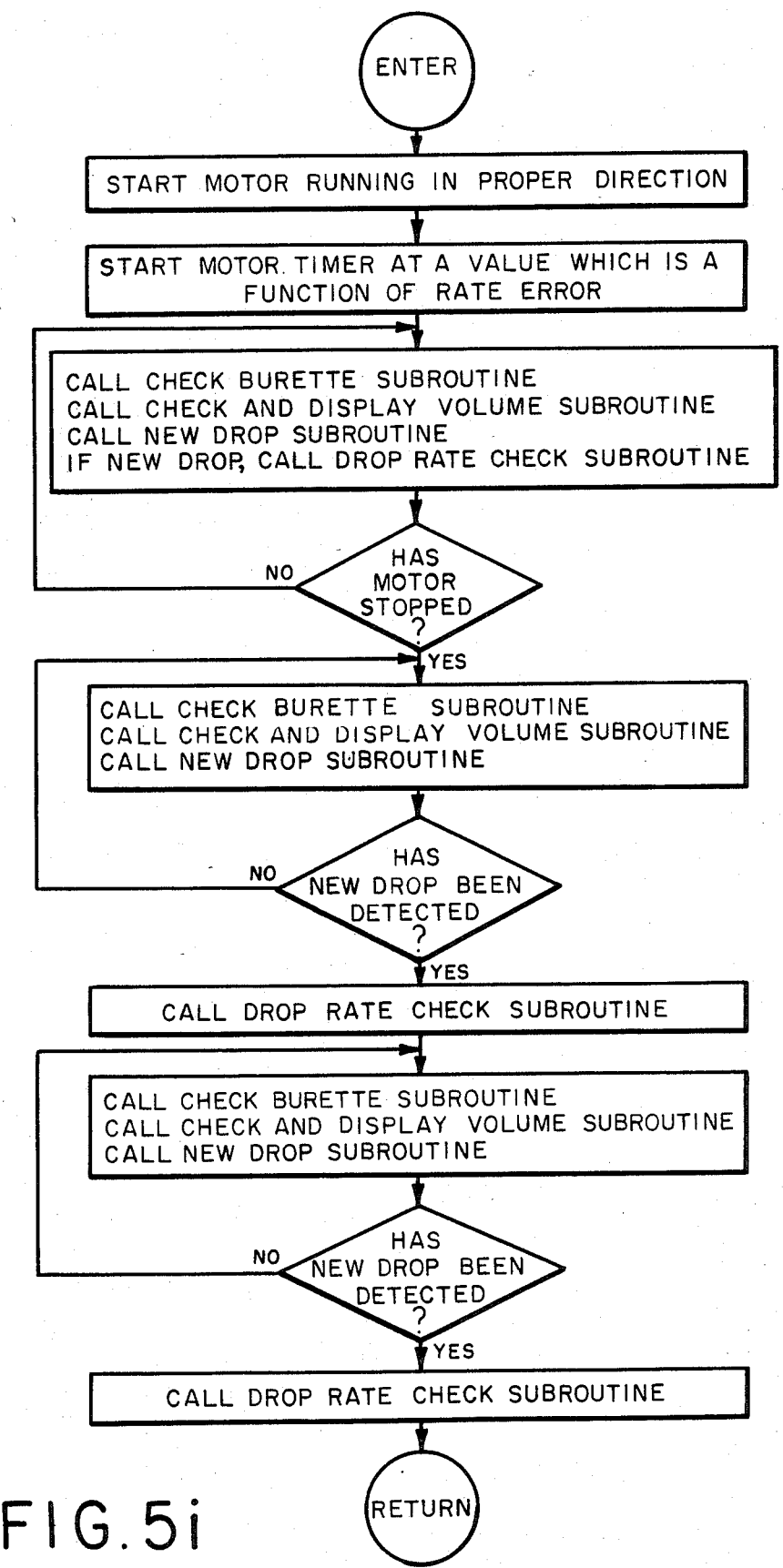

If the rate error is less than 0.99 or greater than 1.01, the Adjust Rate Subroutine of FIG. 5i is then executed. This subroutine starts the motor 84 running in the appropriate direction to bring the actual drop rate equal to the desired drop rate and then sets the motor timer at a value which is a function of the magnitude of the rate error. In general, larger rate errors result in larger initial values for the motor timer. The subroutine waits for the motor to stop, and then waits for two additional drops to be detected in order to allow the system to stabilize. The subroutine then returns.

Figure 5J:
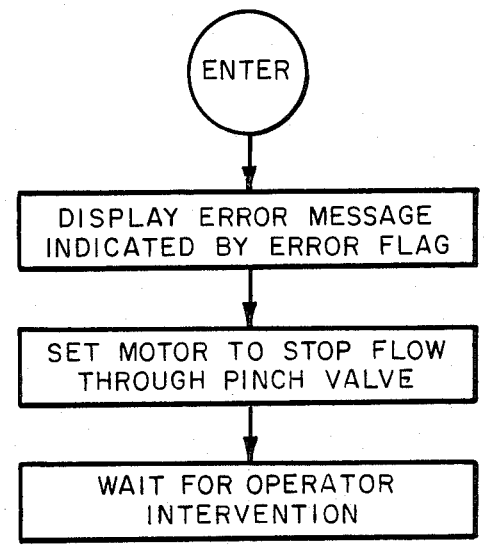

The Error Subroutine shown in FIG. 5j is a simple routine which merely displays the error message indicated by the error flag, sets the motor to stop all flow through the pinch valve, and then waits for intervention by the user.

Figure 5K:
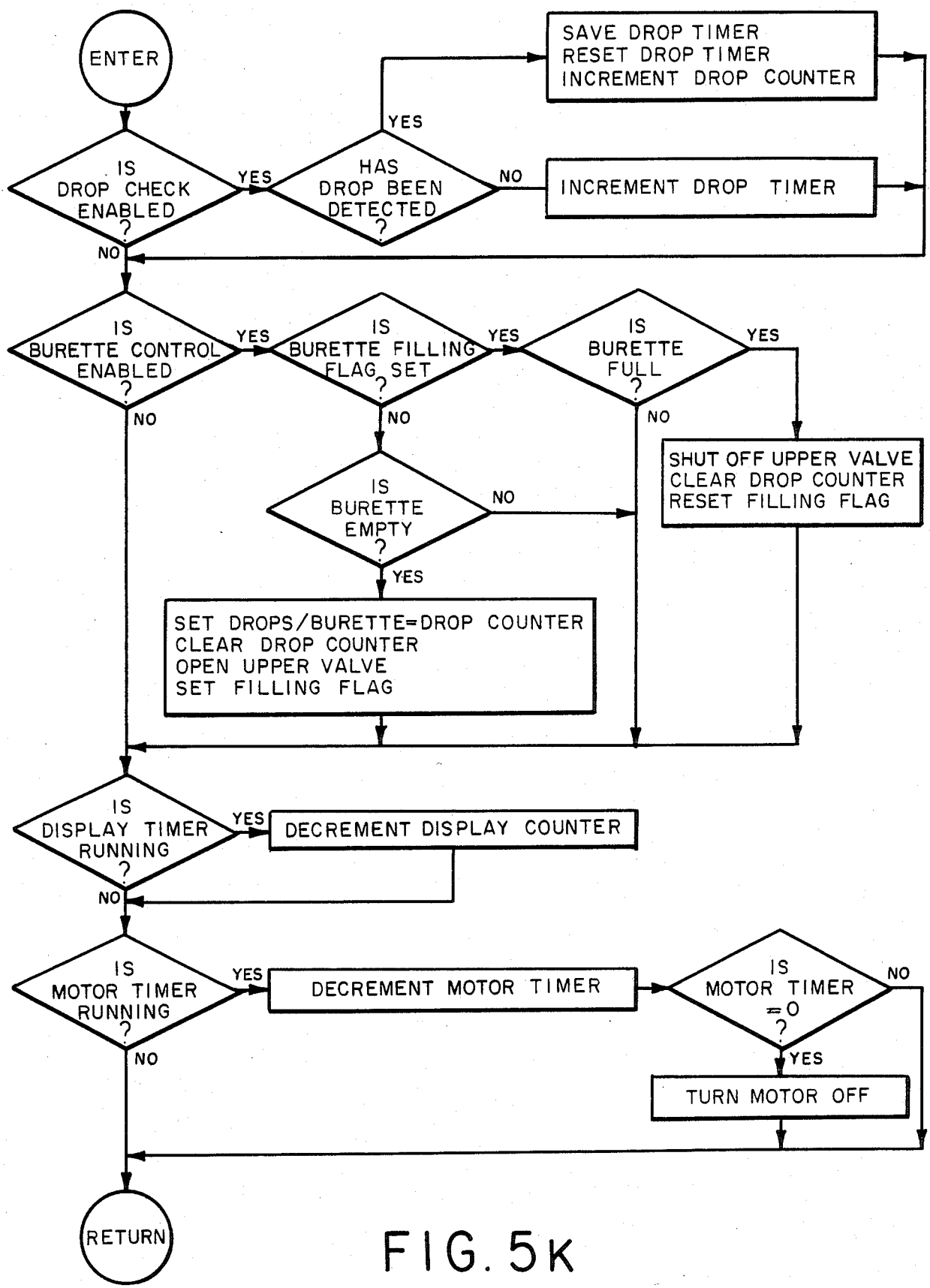

FIG. 5k shows the Interrupt Service Subroutine. This subroutine is executed periodically, at one millisecond intervals. The Interrupt Service Subroutine performs several functions. First, if the drop check function is enabled, the program monitors the output of the drop detector photosensor 90 to determine if a drop has been detected. If so, a drop timer is saved and then reset, and a drop counter is incremented. If no drop has been detected, the drop timer is incremented. In this way, this subroutine acts both to time the period between adjacent drops and to count the total number of drops detected.

The routine of FIG. 5k also provides the burette control function described above. When the burette control function is enabled, the routine of FIG. 5k operates automatically to control the electromagnet 80 to energize the electromagnet 80 when the burette is empty and to deenergize electromagnet 80 when the burette is full. Furthermore, the routine controls relevant drop counters.

When the display timer is running the routine of FIG. 5k decrements the display counter with every pass through the routine. Similarly, when the motor timer is running the routine of FIG. 5k decrements the motor timer and checks to determine if the motor timer is equal to zero. If so, the routine of FIG. 5k turns the motor 84 off, and then returns.

OPERATION

In order to use the controller 10 of this invention, the user snaps an IV set 40 in place in the controller 10 and then presses the Purge key. The controller 10 operates alternately to energize and deenergize the electromagnet 80 to maintain the fluid level in the volumetric chamber 52 between the lower fluid level and the upper fluid level sensors. During this time, fluid is free to drip through the drip chamber 54 to purge the IV set 40. Once the purge has been completed, the user then moves the pinch clamp lever 18 into the closed position. The controller 10 then stops all flow through the pinch valve and operates to fill the volumetric chamber 52 to the upper fluid level. At this point, the cannula or needle can be inserted into the patient and the system is ready to begin operation.

The user then keys in the desired infusion rate and the desired total volume to be infused and presses the Run button. The controller 10 then controls the motor 84 to release the lower pinch clamp to establish an initial drop rate which is determined as a function of a stored assumed volume of each drop.

The electromagnet remains deenergized as the fluid level in the volumetric chamber 52 falls from the upper level to the lower level. During this time, the controller 10 operates automatically to monitor the drop detector photosensor 90 to control the motor 84 to maintain the initial drop rate. Furthermore, the total number of drops detected as the fluid level in the volumetric chamber 52 falls from the upper fluid level to the lower fluid level is counted. The controller then energizes the electromagnet 80 to refill the volumetric chamber 52 to the upper level.

The volume of the volumetric chamber 52 between the upper and lower level is a known quantity, and thus the average volume of each drop can be determined because the total number of drops required to infuse a known volume has been counted. This information is then used to revise the desired drop rate to take into account the currently prevailing volume of individual drops. The motor 84 is then automatically adjusted until the actual flow rate through the housing 48 is very closely equal to the desired flow rate initially entered by the user.

Each time the volumetric chamber 52 empties down to the lower level, the electromagnet 80 is energized to refill the chamber 52. Each time the volumetric chamber 52 empties, the flow rate for the most recently infused ten milliliters is compared to the desired rate set initially, and any slight corrections in the drop rate are made by means of the motor 84. Thus, after the first few tens of milliliters have been infused, the system provides extremely accurate control of the fluid flow rate. In alternate embodiments the controller can operate to measure the time required for the volumetric chamber to empty rather than to count the drops in the chamber in order to determine the actual infusion rate.

When the desired infusion volume has been reached, the controller will go into the KVO mode which is indicated on the display 14. The motor driven pinch clamps slows the drip rate to the KVO rate.

The controller 10 operates to indicate a number of separate errors distinctly and separately. For example, if the container 42 becomes empty during the infusion, the drop rate will fall below the minimum drop rate and the lower level photosensor will indicate that the volumetric chamber 52 is empty. When this condition is detected, the motor is automatically positioned to close off the tube 56 completely to prevent any air from passing to the patient. An audio alarm is sounded and an indicator is lighted on the display 14 indicating that an air in line error has been detected.

In the event of an occlusion such as a kink in the lower tube 56, the drop rate will slow below the minimum drop rate and the lower level photosensor 94 will indicate that the volumetric chamber 52 is not empty. Under these conditions, an audio alarm will be sounded and an indicator will be lighted on the display 14 identifying that an occlusion error has been detected.

In the event that an open line condition occurs (as for example if the needle or cannula pulls out of the patient), the sudden reduction in back pressure will cause the measure drop rate to increase abruptly above the maximum drop rate. This increase in the drop rate is sensed by the controller 10 to activate both an audio alarm and an indication on the display 14 than an open line error has been sensed. Once again, the motor 84 will be driven to cause the clamp to stop all flow through the IV set 40, and thereby to reduce the volume of fluid lost through the open line.

From the foregoing, it should be apparent that a flow control device has been described which is light weight, compact, and relatively inexpensive to manufacture. This controller provides the advantages of extremely accurately controlled flow rate as well as a number of independent alarm modes indicating the exact nature of a number of errors. This controller avoids the inaccuracies of manually controlled drip chambers, and avoids the cost, weight and potential overpressure disadvantages of infusion pumps. It does not require large capacity back-up batteries, for the electronics require little current and the electromagnet and motor are only operated intermittently. Furthermore, this controller provides fail safe operation, for in the event of a power or battery failure, the magnetic valve automatically closes to prevent excessive infusion.

Of course, it should be understood that various changes and modifications of the preferred embodiments described above will be apparent to those skilled in the art. For example, a wide range of computers and a wide range of specific programs can be used to implement the disclosed functions, and stored parameters can readily be adjusted for individual applications. Furthermore, this invention is not limited to photosensitive means for detecting drop formation and fluid level in the IV set. In alternate embodiments conductive or capacitive sensors can be used as well. As described above, a wide range of valves and means for interrupting flow into the volumetric chamber can be used, and the geometry of the volumetric chamber and the drip chamber can be varied widely as well. Depending on the precise geometry chosen, it may be preferable to form the conduit 70 integrally with one of the walls of the volumetric chamber, or even to position the conduit 70 outside of the volumetric chamber. In addition, the controller 10 may be implemented with analog rather than digital electronics.

It is therefore intended that the foregoing detailed description be regarded as illustrative rather than limiting, and that it be understood that it is the following claims, including all equivalents, which are intended to define the scope of this invention.

We claim:

1. A flow control device for use with an intravenous set comprising a drip chamber, a volumetric chamber having a predetermined volume connected to the drip chamber, and externally actuated means for selectively interrupting fluid flow into the volumetric chamber, said flow control device comprising:

means for measuring a drop rate indicative of the rate of drop formation in the drip chamber;

means for designating a selected volumetric flow rate;

means for designating a selected drop rate;

means for storing the selected volumetric flow rate;

means for automatically controlling fluid flow out of the drip chamber to cause the measured drop rate in the drip chamber to approach the selected drop rate;

means for automatically actuating the interrupting means to cause the volumetric chamber to fill and empty repeatedly such that said volumetric chamber repeatedly dispenses said predetermined volume; and means for automatically and repeatedly measuring the rate at which the volumetric chamber empties to determine a parameter indicative of the volumetric flow rate of fluid out of the volumetric chamber and for automatically modifying the selected drop rate in response to said parameter to cause the volumetric flow rate of fluid out of the drip chamber to approach the selected volumetric flow rate.

2. The invention of claim 1 wherein the intravenous set further comprises a deformable tube coupled to the drip chamber to conduct fluid therefrom, and wherein the means for controlling fluid flow comprises a pinch member situated to contact the deformable tube, and means for positioning the pinch member to deform the tube to control the rate of fluid flow through the tube.

3. The invention of claim 1 wherein the means for selectively interrupting fluid flow comprises a magnetically responsive valve member, and wherein the means for actuating the interrupting means comprises an electromagnet.

4. The invention of claim 1 wherein the actuating means comprises:

upper and lower light sources positioned at upper and lower levels, respectively, with respect to the volumetric chamber; and upper and lower photodetectors positioned at the upper and lower levels, respectively;

said upper light source and upper photodetector forming an upper detection system for detecting when fluid in the volumetric chamber reaches the upper level;

said lower light source and lower photodetector forming a lower detection system for detecting when fluid in the volumetric chamber reaches the lower level.

5. The invention of claim 1 further comprising:

means for activating an occlusion alarm in the event of the measured drop rate decreases to an insufficient flow alarm rate, less than the selected rate, when the fluid level in the volumetric chamber is above a first level; and means for activating an inadequate supply alarm, separate from the occlusion alarm, in the event the volumetric chamber fails to fill to a selected level.

6. The invention of claim 1 or 5 further comprising:

means for activating an excessive flow alarm in the event the measured drop rate increases to an excessive flow alarm rate, greater than the selected drop rate.

7. The invention of claim 1 wherein the means for selectively interrupting fluid flow comprises a collapsable conduit and wherein the means for actuating the interrupting means comprises an adjustable pinch clamp positioned to pinch the collapsable conduit.

8. A flow control device for use with an intravenous set comprising a drip chamber, a volumetric chamber connected to the drip chamber, and externally actuated means for selectively interrupting fluid flow into the volumetric chamber, said flow control device comprising:

a frame;

means for mounting the drip chamber, the volumetic chamber, and the interrupting means to the frame;

means for controlling the fluid flow out of the drip chamber;

means for detecting drops formed in the drip chamber;

means for determining when the fluid level in the volumetric chamber fails to a lower level;

means for determining when the fluid level in the volumetric chamber rises to an upper level;

means for actuating the interrupting means;

a computer coupled to the controlling means, the detecting means, the lower level determining means, the upper level determining means, and the actuating means;

means, included in the computer, for storing a requested flow rate;

means, included in the computer, for controlling the actuating means to fill the volumetric chamber to the upper level;

means, included in the computer, for causing the means for controlling fluid flow out of the drip chamber to establish a first drop rate selected to provide a first approximation of the requested flow rate;

means, included in the computer, for counting the drops detected as the fluid level in the volumetric chamber falls from the upper level to the lower level to determine a parameter indicative of the actual flow rate; and means, included in the computer, for causing the means for controlling fluid flow out of the drip chamber to establish a second drop rate which differs from the first drop rate in correspondence to the discrepancy between the actual flow rate and the requested flow rate to provide a second approximation of the requested flow rate which is closer to the requested flow rate than is the first approximation of the requested flow rate.

9. The invention of claim 8 wherein the interrupting means comprises a magnetically responsive valve member and wherein the actuating means comprises an electromagnet.

10. The invention of claim 8 wherein the drop detecting means comprises a photodetector situated to detect the passage of individual drops.

11. The invention of claim 8 wherein the upper and lower level determining means comprise respective photodetectors situated to detect fluid levels at the upper and lower levels, respectively.

12. The invention of claim 8 wherein the means for controlling fluid flow out of the drip chamber comprises:
a pinch clamp; and
means for adjusting the pinch clamp.

13. The invention of claim 8 further comprising:
means, included in the computer, for activating an occlusion alarm in the event the measured drop rate falls below an insufficient flow alarm drop rate, lower than the second drop rate, and fluid is present at a selected level in the volumetric chamber; and
means, included in the computer, for activating an inadequate supply alarm, separate from the occlusion alarm, in the event the measured drop rate falls below the insufficient flow alarm drop rate and fluid is not present at the selected level in the volumetric chamber.

14. The invention of claim 8 or 13 further comprising:
means, included in the computer, for activating an excessive flow alarm in the event the measured drop rate exceeds an excessive flow alarm rate, greater than the second drop rate.

15. The invention of claim 7 wherein the interrupting means comprises a collapsable conduit, and wherein the actuating means comprises an adjustable pinch clamp positioned to pinch the collapsable conduit.

16. A flow control device for use with an intravenous set comprising a drip chamber, a volumetric chamber connected to the drip chamber, and externally actuated means for selectively interrupting fluid flow into the volumetric chamber, said flow control device comprising:
a frame;
means for mounting the drip chamber, the volumetric chamber, and the interrupting means to the frame;
means for controlling fluid flow out of the drip chamber;
means for detecting drops formed in the drip chamber;
means for determining when the fluid level in the volumetric chamber falls to a lower level;
means for determining when the fluid level in the volumetric chamber rises to an upper level;
means for actuating the interrupting means;
a computer coupled to the controlling means, the detecting means, the lower level determining means, the upper level determining means, and the actuating means;
means, included in the computer, for storing a requested flow rate;
means, included in the computer, for causing the controlling means to establish a first drop rate selected to provide a first approximation of the requested flow rate;
means, included in the computer, for determining the rate at which the fluid level in the volumetric chamber falls from the upper level to the lower level to determine a parameter indicative of the actual flow rate; and
means, included in the computer, for causing the controlling means to establish a second drop rate which differs from the first drop rate in correspondence to the discrepancy between the actual flow rate and the requested flow rate to provide a second approximation of the requested flow rate which is closer to the requested flow rate than is the first approximation of the requested flow rate.

17. The invention of claim 16 wherein the interrupting means comprises a magnetically responsive valve member and wherein the actuating means comprises an electromagnet.

18. The invention of claim 16 wherein the drop detecting means comprises a photodetector situated to detect the passage of individual drops.

19. The invention of claim 16 wherein the upper and lower level determining means comprise respective photodetectors situated to detect fluid levels at the upper and lower levels, respectively.

20. The invention of claim 16 wherein the controlling means comprises:
a pinch clamp; and
means for adjusting the pinch clamp.

21. The invention of claim 16 further comprising:
means, included in the computer, for activating an occlusion alarm in the event the measured drop rate falls below an insufficient flow alarm drop rate, lower than the second drop rate, and fluid is present at a selected level in the volumetric chamber; and
means, included in the computer, for activating an inadequate supply alarm, separate from the occlusion alarm, in the event the measured drop rate falls below the insufficient flow alarm drop rate and fluid is not present at the selected level at the volumetric chamber.

22. The invention of claim 16 or 21 further comprising:
means, included in the computer, for activating an excessive flow alarm in the event the measured drop rate exceeds an excessive flow alarm rate, greater than the second drop rate.

23. The invention of claim 16 wherein the interrupting means comprises a collapsable conduit and wherein the actuating means comprises an adjustable pinch clamp positioned to pinch the collapsable conduit.

* * * * *

UNITED STATES PATENT AND TRADEMARK OFFICE
CERTIFICATE OF CORRECTION

PATENT NO. : 4,525,163
DATED : June 25, 1985
INVENTOR(S) : William H. Slavik and William B. Huber It is certified that error appears in the above-identified patent and that said Letters Patent is hereby corrected as shown below:

In claim 5 (column 14, line 7), please delete "of";

In claim 15 (column 15, line 37), please delete "claim 7" and substitute therefor --claim 8--;

In claim 21 (column 16, line 48), please delete "at" (second occurrence) and substitute therefor --in--.

Signed and Sealed this

Twenty-first Day of October, 1986

[SEAL]

Attest:

DONALD J. QUIGG

Attesting Officer     Commissioner of Patents and Trademarks